(12) United States Patent
Levite et al.

(10) Patent No.: US 8,859,001 B2
(45) Date of Patent: Oct. 14, 2014

(54) FENOLDOPAM FORMULATIONS AND PRO-DRUG DERIVATIVES

(76) Inventors: Mia Levite, Savyon (IL); Avi Domb, Efrat (IL)

( * ) Notice: Subject to any disclaimer, the term of this patent is extended or adjusted under 35 U.S.C. 154(b) by 953 days.

(21) Appl. No.: 12/738,781

(22) PCT Filed: Oct. 20, 2008

(86) PCT No.: PCT/US2008/080495
§ 371 (c)(1),
(2), (4) Date: Jan. 18, 2011

(87) PCT Pub. No.: WO2009/052491
PCT Pub. Date: Apr. 23, 2009

(65) Prior Publication Data
US 2011/0104287 A1    May 5, 2011

Related U.S. Application Data

(60) Provisional application No. 60/980,842, filed on Oct. 18, 2007.

(51) Int. Cl.
| | |
|---|---|
| *A61K 9/14* | (2006.01) |
| *A61K 9/20* | (2006.01) |
| *A61K 31/55* | (2006.01) |
| *A61K 47/48* | (2006.01) |
| *C07D 223/16* | (2006.01) |
| *A61K 47/34* | (2006.01) |
| *A61K 9/51* | (2006.01) |
| *A61K 9/107* | (2006.01) |
| *A61K 9/00* | (2006.01) |
| *B82Y 5/00* | (2011.01) |

(52) U.S. Cl.
CPC ......... *A61K 9/1075* (2013.01); *A61K 47/48215* (2013.01); *C07D 223/16* (2013.01); *A61K 47/48046* (2013.01); *A61K 47/34* (2013.01); *A61K 9/5153* (2013.01); *A61K 47/4823* (2013.01); *A61K 9/0019* (2013.01); *A61K 31/55* (2013.01); *A61K 47/488* (2013.01); *A61K 9/0024* (2013.01); *B82Y 5/00* (2013.01)
USPC ........... 424/489; 424/401; 424/464; 424/449; 540/595; 564/388

(58) Field of Classification Search
CPC ......... A61K 9/20; A61K 9/16; A61K 9/2013; A61K 9/1075; A61K 9/127; A61K 8/68; A61K 8/30; A61K 8/02; A61K 9/50; A61K 31/55; C07D 223/00
See application file for complete search history.

(56) References Cited

U.S. PATENT DOCUMENTS

| | | | |
|---|---|---|---|
| 4,861,771 A * | 8/1989 | Gaitanopoulos et al. | 514/217.02 |
| 6,238,693 B1 * | 5/2001 | Luther et al. | 424/448 |
| 6,699,497 B1 * | 3/2004 | van Osdol et al. | 424/448 |
| 8,246,978 B2 * | 8/2012 | Kydonieus et al. | 424/448 |
| 2004/0220081 A1 * | 11/2004 | Kreitz et al. | 514/2 |
| 2011/0071204 A1 * | 3/2011 | Takahashi et al. | 514/399 |

OTHER PUBLICATIONS

Film-forming agent. Wikipedia. 1 page, Apr. 8, 2013.*

* cited by examiner

*Primary Examiner* — Lakshmi Channavajjala
(74) *Attorney, Agent, or Firm* — Browdy and Neimark, PLLC

(57) ABSTRACT

Formulations of fenoldopam are disclosed for repeated administration or continued slow release administration, over prolonged periods of time or targeted slow and regulated delivery. The formulations include those formulations that increase the bioavailability of fenoldopam after oral intake, particularly lipid based nano dispersions and pronanodispersions and surfactant rich formulations. This may be accomplished by entrapment in nanoparticles or liposomal formulations or conjugation to a polymer or small molecule via a soft bond.

21 Claims, No Drawings

FENOLDOPAM FORMULATIONS AND PRO-DRUG DERIVATIVES

FIELD OF THE INVENTION

The present invention generally relates to the use of new fenoldopam formulations and prodrug derivatives for oral, parenteral, nasal, topical, transdermal, or intratissue administration, particularly for repeated administration or continued slow release administration, over prolonged periods of time or targeted slow and regulated delivery. The formulations include those formulations that increase the bioavailability of fenoldopam after oral intake, particularly lipid based nanodispersions and pronanodispersions and surfactant rich formulations. This invention also includes dermal formulations for the purpose of localizing the drug to the infected area on the skin with minimal systemic administration. This invention also includes injectable and implantable formulations that release fenoldopam at a controlled rate to the surrounding tissue for periods of days to months. This invention also includes intravenous formulations where fenoldopam is entrapped in nanoparticles or liposomal formulations or conjugated to a polymer or small molecule via a soft bond so that after administration to the body the drug is released as a function of the cleavage rate of the conjugation bond, thus extending their stability and circulation time in the blood system. This is achieved by encapsulation in a biodegradable polymer, such as PLA, or entrapment in a liposomal or a liposphere type of dispersion. The encapsulated fenoldopam entity may contain a hydrodynamic surface, such as PEG chains, which reduces RAS ability to eliminate the drug from the blood stream. Fenoldopam can also be administered within a solid tumor or localized at an inflamed tissue or delivered systemically from an implant. Fenoldopam is used in this invention also for conjugation of particles or agents to cells rich with fenoldopam-interacting receptors and binding sites on the cell surfaces. Magnetic particles with surface bound fenoldopam are used for separation of infected cells or delivery of drug loaded particles to infected cells. These fenoldopam formulations have applications in the eradication of cancer cells or TCR-activated autoimmune cells or chronically-activated inflammatory or detrimental TCR-activated graft rejecting T-cells (i.e., the cells that reject a foreign organ transplanted to or within a body of a human being or animal, such as liver, kidney, heart, lung, bone, etc.), or detrimental TCR-activated T-cells causing Graft Versus Host Disease (GVHD) or any other detrimental cells that express high or even moderate cell surface concentration of dopamine D1 receptors (D1R) to which fenoldopam binds with very high selectivity, and subsequently kills these detrimental cells. Such novel fenoldopam formulations are needed for achieving repeated or sustained exposure (as in a chronic disease) or targeted and regulated delivery and binding of fenoldopam to the cancer or the other detrimental cells, to achieve the maximal killing of these disease-causing or disease-facilitating cells each time they are present in the body, and each time they may re-proliferate or penetrate specific organs, rather than the currently clinically-used fenoldopam formulation suitable and approved by the medical regulatory agencies (e.g. FDA) for one intravenous systemic administration for acute pathological condition: acute hypertension.

BACKGROUND OF THE INVENTION

This application is related to PCT publication WO2007019266, entitled "KILLING HUMAN LYMPHOMA AND LEUKEMIA CANCER CELLS AND TCR-ACTIVATED NORMAL HUMAN CELLS BY DOPAMINE D1R AGONISTS" (the inventor of which, Dr. Mia Levite, being one of the present inventors), the entire contents of which are hereby incorporated herein by reference. This PCT publication discloses the unexpected activity of fenoldopam mesylate as a drug that potently and rapidly kills cancer cells, and specifically various types of human leukemia and lymphoma of T-cell or B-cell or non-T non-B origin, that express the D1R on their cell surface, thereby revealing the unknown ability of fenoldopam mesylate to act as an anti-cancer agent.

In PCT publication WO2007019266, the following findings are described:

1) Some types of human and mouse lymphoma (among them several types of T-cell lymphoma and leukemia (among them T-cell leukemia)) have moderate-dramatic elevation in the levels of dopamine D1 receptors expressed on their cell surface, in contrast to normal (i.e., non cancerous) human resting peripheral T-cells, which express negligible levels, if at all, of D1 dopamine receptors.

2) Exposing in vitro five different types of T-cell, B-cell or myeloid type human lymphoma and leukemia lines (specifically, the T-cell leukemia line, Jurkat; the human T-lymphoma line, the HuT-78 cutaneous 'Sezary' T-lymphoma; the human Chronic-Myeloid Leukemia (CML) line, K-562; and the human B-lymphoma lines: Burkitt's lymphoma lines Daudi and Raji) to concentration range of 1 mM-0.01 mM of fenoldopam mesylate or to several concentrations of other highly selective D1R agonists, leads to the death of all, or the vast majority of, these cancer cells.

The selective dopamine D1/5 receptor agonists tested and found effective in killing lymphoma and leukemia are: (1R-cis)-1-(aminomethyl)-3,4-dihydro-3-tricyclo[3.3.1.13,7]dec-1-yl-[1H]-2-benzopyran-5,6-diol hydrochloride (TOCRIS Cookson Product name: A 77636 hydrochloride; Catalog number: 1701; referred to as "potent, selective D1-like agonist; orally active"), (±)-1-phenyl-2,3,4,5-tetrahydro-(1H)-3-benzazepine-7,8-diol hydrobromide (TOCRIS COOKSON Product name: SKF 38393 hydrobromide; Catalog number: 0922; referred to as "D1-like dopamine receptor selective partial agonist"), and cis-(±)-1-(aminomethyl)-3,4-dihydro-3-phenyl-1H-2-benzopyran-5,6-diol hydrochloride (TOCRIS COOKSON Product name: 1534; Catalog number: A 68930 hydrochloride; referred to as "potent and selective D1-like dopamine receptor agonist").

3) The killing of lymphoma and leukemia by fenoldopam mesylate and all the other selective dopamine D1/5 receptor agonists is dose dependent. Nevertheless, as expected, some D1R agonists were much more effective than others, and could kill the cancer cells in lower concentrations than the others. Fenoldopam mesylate and A 77636 hydrochloride were the most effective cancer killers and are thus preferred embodiments for use in the present invention.

4) Cell death induced by the fenoldopam mesylate or other highly specific dopamine D1R agonists is rapid (starting and measurable within 1-60 minutes after exposure), and occurred primarily via a mechanism of necrosis.

5) Most of the lymphoma and leukemia cells tested expressed on their cell surface markedly elevated levels not only of the D1R, but also of the dopamine D3 and dopamine D2 receptors, compared to much lower cell surface expression of the respective receptors on normal (not cancer) human T-cells. Yet, dopamine D2 and D3 receptor agonists exhibited much lower anti-cancer killing activity, if at all, compared to the effect exerted by the dopamine D1R agonists.

In PCT publication WO2007019266, it is further claimed that the findings described therein are relevant to novel treatment not only of cancers that express the D1R, but also to the treatment of diseases caused by activated T-cells, among them being, for example, T-cell mediated autoimmune diseases, T-cell mediated inflammatory diseases, T-cell mediated graft rejection and T-cell mediated Graft Versus Host Diseases (GVHD), the two latter occurring after mis-matched organ or cell transplantation. This is claimed based in the following findings also described in PCT publication WO2007019266:

A. T-cell receptor (TCR)-activated normal (i.e., non cancerous) human peripheral T-cells express dramatically elevated levels of dopamine D1 receptors on their cell surface, as opposed to resting normal human peripheral T-cells that do not express this receptor, or do so to minimal not significant levels.

B. Exposing TCR-activated human normal peripheral T-cells in vitro to several highly selective dopamine D1R agonists, such as fenaldopam mesylate, kills potently a substantial proportion of these activated T-cells, while hardly affecting the resting (i.e., not TCR-activated) human normal peripheral T-cells. The killing of TCR-activated T-cells by all the selective dopamine D1R agonists is dose dependent, as seen for the killing of cancer cells, and also, here, as expected, some D1R agonists are much more effective than others, and could kill the cancer cells in lower concentrations than the others. Of all the highly selective D1R agonists tested therein, fenoldopam mesylate and A 77636 hydrochloride were the most effective killers of TCR-activated T-cells.

Thus, the findings described in PCT publication WO2007019266 reveal the previously unknown ability of fenoldopam mesylate to kill not only cancer cells of T, B and non-T non-B origin (CML being an example of the latter type), that express D1R, but also to kill non-cancerous normal (yet potentially causing other diseases than cancer) TCR-activated human T-cells, while causing only minimal death of resting normal human T-cells. These findings suggest that fenoldopam can potentially act not only as a drug for D1R expressing cancers, but also as a drug for T-cell mediated (or T-cell associated) autoimmune diseases, as in such diseases the damage is caused by TCR-activated T-cells that are directed towards a specific self antigen and are activated by such autoantigen over and over again.

The following is a list of all accepted autoimmune diseases, each of which is expected to be treatable by means of the present invention: acute disseminated encephalomyelitis (ADEM), Addison's disease, ankylosing spondylitis, antiphospholipid antibody syndrome (APS), aplastic anemia, autoimmune hepatitis, autoimmune oophoritis, coeliac disease, Crohn's disease, diabetes mellitus type 1, gestational pemphigoid, Goodpasture's syndrome, Graves' disease, Guillain-Barré syndrome, Hashimoto's disease, idiopathic thrombocytopenic purpura, Kawasaki's disease, lupus erythematosus, multiple sclerosis, myasthenia gravis, opsoclonus myoclonus syndrome (OMS), optic neuritis, Ord's thyroiditis, pemphigus, pernicious anaemia, polyarthritis in dogs, primary biliary cirrhosis, rheumatoid arthritis, Reiter's syndrome, Sjögren's syndrome, Takayasu's arteritis, temporal arteritis (also known as "giant cell arteritis"), warm autoimmune hemolytic anemia, and Wegener's granulamatosis. The following is a list of diseases suspected or theorized to be linked to autoimmunity, each of which are expected to be treatable by means of the present invention: alopecia universalis, Behçet's disease, Chagas' disease, chronic fatigue syndrome, dysautonomia, endometriosis, hidradenitis suppurativa, interstitial cystitis, Lyme disease, morphea, neuromyotonia, narcolepsy, psoriasis, sarcoidosis, schizophrenia, scleroderma, ulcerative colitis, vitiligo, and vulvodynia.

In general, the autoimmune diseases can be broadly divided into systemic and organ-specific or localized autoimmune disorders, depending on the principal clinico-pathologic features of each disease.

A partial list of human T-cell mediated autoimmune diseases, each of which is expected to be treatable by means of the present invention, includes the following: insulin-dependent (type 1) diabetes mellitus, multiple sclerosis, myasthenia gravis, autoimmune myocarditis, alopecia aerate (the latter now understood to represent an organ-restricted, T cell-mediated autoimmune disease of hair follicles), and others.

Fenoldopam mesylate was also suggested in PCT publication WO2007019266 to act against anti-inflammatory diseases, or against any other disease in which the detrimental cells express the D1R, and whereby the binding of this receptor by fenoldopam mesylate kills these cells.

The inflammatory diseases are disease characterized by inflammation. These diseases, each of which is expected to be treatable by means of the present invention, are listed in: www.thefreedictionary.com/inflammatory+disease.

TCR-activated T-cells are also detrimental in cases of organ transplantation, as they are the cells that recognize the transplanted organ as foreign and reject it, as well as in cases of GVHD, as they are the transplanted cells that recognize the new body as foreign, and attack it.

Based on the ability of fenoldopam to eradicate TCR-activated T-cells, described in PCT publication WO2007019266, while sparing resting T-cells, it is suggested therein to potentially act also as an anti-graft rejection drug, and thus to prevent the rejection of transplanted organs or cells, as well as an anti-GVHD drug, and thus prevent the devastating consequences of this disease, which often kills the transplanted patient.

Fenoldopam mesylate has a very short half life: $T_{1/2}$=~5 min, and is rapidly eliminated upon discontinuation of the IV infusion.

While fenoldopam mesylate is currently used in the clinic in an FDA-approved protocol of a single 24 hr-48 hr IV administration for acute hypertension, other new formulations are needed to get an optimal effect for its new indications, including anti-cancer, anti-autoimmune, anti-inflammatory, anti-graft rejection, and anti-GVHD agent. For all these new indications, it may be of high advantage to have in hand a drug formulation that can be given at multiple times, or that is released slowly and continuously over periods from a few hours to a few weeks or months, or with a longer half life in the body, or that can be injected locally into the tumor or into autoimmune-afflicted organs and released therein over a desired period in a regulated manner, and/or suitable for treatment of a chronic pathological condition (rather than acute one) or other.

Fenoldopam mesylate (6-chloro-2,3,4,5-tetrahydro-1-(4-hydroxyphenyl)-1H-3-benzazepine-7,8-diol, methanesulfonate) is a highly selective agonist for the dopamine D1 receptor (termed D1R receptor or dopamine DA1 agonist), causing an increased splanchnic and renal blood flow with a strong diuretic and natriuretic effect. It possesses several decisive advantages as an antihypertensive and for the treatment of congestive heart failure over commonly used other drugs.

Fenoldopam mesylate is used in the clinic for its vasodilatory actions mainly in the treatment of severe hypertension. It has only peripheral actions and does not cross the blood-brain barrier (BBB). The major side effects reported in 10% (or less) of the patients are headache, flushing and nausea The solubility of fenoldopam mesylate is 9.1 mg/ml in an HCl/KCl buffer pH 1.5, but decreases to 0.13 mg/ml in buffer pH 6.8 and to 0.06 mg/ml in pH 7.5. Free base fenoldopam is hydrophobic and can be incorporated in a formulation for improved drug load and release profile. Fenoldopam is a white to off-white powder with a molecular weight of 401.87 and a molecular formula of C16H16ClNO3.CH3SO3H. It is sparingly soluble in water, ethanol and methanol, and is soluble in propylene glycol. Ampules for injection contain in each 1 mL in sterile aqueous solution, citric acid 3.44 mg; fenoldopam mesylate equivalent to fenoldopam 10 mg; propylene glycol 518 mg; sodium citrate dihydrate 0.61 mg; sodium metabisulfite 1 mg (Formula 1).

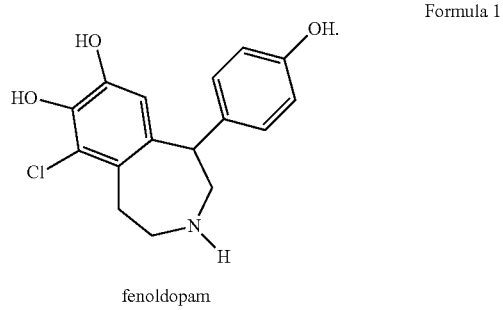 [SMILES: Oc1ccc(C2CNCCc3c2cc(O)c(O)c3Cl)cc1]

Formula 1 fenoldopam

This infusion is given only at acute situations to treat blood pressure disorders or problems of patients, primarily those suffering from kidney disorders or problems.

There are no other clinical formulations for this drug, not an oral or even a non-infused parenteral formulation. There are a few patents describing tablet type formulations for oral use and transdermal delivery. U.S. Pat. Nos. 6,238,693 and 6,960,353 describe compositions for application to skin to administer fenoldopam by permeation through the skin, using a permeation enhancer and hydrogels. The disclosed transdermal application of fenoldopam is for the treatment of hypertension, congestive heart failure, and chronic and acute renal failure. Moreover, these formulations did not address formulation issues such as limited solubility of fenoldopam which requires the development of specific formulations for poorly soluble drugs. Moreover, this drug possesses ortho-resorcinol groups which are highly sensitive to oxidation, and with limited stability in general. Also, formulations for extended release were not described for this drug, other than one publication which describes a coated tablet for oral administration releasing fenoldopam and succinic acid for a few hours in vitro (European Journal of Pharmaceutics and Biopharmaceutics, 46:105-113 (1998)).

SUMMARY OF THE INVENTION

It is therefore an object of this invention to provide non-infusion formulations for non-acute conditions, suitable for oral, topical transdermal and injectable administration.

It is further an object of this invention to provide suitable extended controlled release formulations for fenoldopam.

It is a further object of this invention to provide pharmaceutical formulations where fenoldopam is kept stable through the process of preparation, storage and administration.

It is yet another object of this invention to provide pharmaceutical formulations with improved oral bioavailability.

It is another object of the present invention to provide iv injectable formulations with improved stability and longer drug action, preferably with the fenoldopam in the form of nanolipospheres.

It is a further object of the present invention to provide intra-tissue controlled release formulations for systemic delivery or for localized delivery, particularly site specific delivery that is intratumoral or intra-inflammatory tissue.

It is yet a further object of this invention to provide pharmaceutical implants, delivered by injection or implantation, that release effective doses of fenoldopam for periods from days to months in tissue for systemic or localized delivery.

It is yet another object of this invention to provide effective and convenient fenoldopam pharmaceutical formulations suitable for treating cancer, or inflammatory, or immune and autoimmune disorder patients, and patients suffering from graft rejection and/or GVHD after organ or cell transplantation.

It is still a further object of this invention to provide fenoldopam derivatives that are superior to native fenoldopam in terms of stability, extended activity, biodistribution, ease of formulation, reduced toxicity, penetration through biological membranes, such as the skin, the blood brain barrier, and the gastrointestinal tract, and with a wider therapeutic window.

It is another object of this invention to provide prodrug derivatives where the phenolic groups are esterified, carbonated or etherified with organic residues that are cleaved after administration to the body into native active fenoldopam.

It still another object of this invention to provide prodrug derivatives where the amino group is connected or complexed with organic residues that are cleaved after administration to the body into native active fenoldopam.

It yet a further object of this invention to provide metal ion and salt complexes of the phenolic groups or amino group to provide fenoldopam with improved activity.

It is a further object of this invention to provide fenoldopam conjugates to a particle surface or an agent for conjugation to cells rich with fenoldopam receptors for cell sorting for therapeutic effect, cell separation when using magnetic particles, or targeted drug delivery. This can include magnetic nanoparticles with active fenoldopam on the surface for in vitro cell sorting and separation for treatment or for diagnostics.

One of the principles of this invention is the preparation of fenoldopam formulations that allow optimal administration of fenoldopam to the body for the treatment of cancer or immune and autoimmune disorder patients, and patients suffering from graft rejection and/or GVHD after organ or cell transplantation or any other pathological conditions whereby the disease-causing or disease-facilitating detrimental cells express the dopamine receptor D1R, and whereby such detrimental cells can be killed rapidly and potently by exposure to fenoldopam or other D1R agonist. Thus, such novel fenoldopam formulations can be of novel therapeutic value to arrest the respective above-mentioned diseases and others.

This is achieved by either formulating the drug into pharmaceutical nanoparticulate and polymer based formulations or by modifying the drug by either temporarily covalently binding a hydrophilic or hydrophobic residue to one or more of the phenolic hydroxyl groups or the secondary amine group, or by forming salts with the phenolic groups with biocompatible bases, or forming a salt with an acid via the secondary amine group of the drug.

The alternatives for chemical modification of the drug are given in the following Scheme.

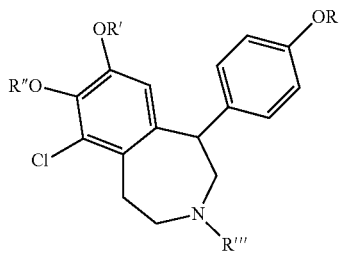

wherein R, R' and R" are the same or different residues that form an electrostatic salt with the phenolate anion, a metal ion or organometallic molecules that form a complex with one or more phenolic groups, or an organic residue covalently bound to the phenolic residue via a bio-cleavable bond such as an ester, or carbonate bond; and R''' is a specific residue that forms an electrostatic salt with the amine, a metal ion or atom or an organic residue covalently bound to the amino residue via a bio-cleavable bond, such as an amine, amide, or urea bond.

New formulations of fenoldopam, as free drug or salt, developed in this invention that are suitable for the parenteral, intratumoral and nasal delivery of fenoldopam, are based on the liposphere particulate formulations that are nano- or micro-dispersions in aqueous media. Another group of formulations are based on ingredients that are in the solution that solubilize the drug by forming electrostatic interactions with the ingredients. Such formulations include solutions of a biocompatible polycation, such as amino acids and lysine-containing peptides, chitosan, that may interact with the phenolic residues, or acidic derivatives such as hyaluronic acid, alginic acid, and carboxy methyl cellulose (CMC) that may interact with the secondary amine of fenoldopam.

Synthesis of novel lipophilic prodrugs of fenoldopam having high affinity to lipids and chilomicrons may be dispersed well in aqueous solution with the aid of a surfactant to provide injectable long acting formulations. Alternatively, the association with chylomicrons potentially reduces the hepatic metabolism of the lipophilic prodrug of fenoldopam by targeting the prodrug loaded chylomicrons to the lymph instead of to the portal blood. Novel methods for determining the degree of association with chylomicrons of drugs as well as for quantification of the degree of intestinal lymphatic transport in in vivo models have been developed.

The compounds with high affinity to chylomicrons exhibit a high degree of intestinal lymphatic transport, thereby bypassing the liver during absorption following oral administration. Thus, the degree of hepatic first-pass metabolism is significantly reduced or completely eliminated in this route of absorption and the total oral bioavailability is significantly increased. As a result, it is possible to administer these novel molecules orally with the appropriate lipid based formulation that contains long chain (~$C_{12-20}$, e.g., oleic acid) fatty acids or long chain triglyceride (~$C_{12-20}$, e.g., peanut oil). The chemical binding is designed in such a way to allow the bond between fenoldopam and the lipophilic chain to undergo bond dissociation in the systemic circulation by plasma enzymes. This dissociation increases the bioavilability of the drug.

Formulations:

The use of dispersion systems as carriers of biologically active compounds is well known in the art. These systems are designed to protect the biologically active compound from the environment during delivery and to provide a controlled release of the substance to a targeted area. In some cases, the goal is to target specific sites in the body using the dispersion. Alternatively, the drug carrier system acts as a reservoir at the site of injection.

Dispersion systems used for pharmaceutical and cosmetic formulations can be categorized as either suspensions or emulsions. Suspensions are defined as solid particles ranging in size from a few nanometers up to hundreds of microns dispersed in an aqueous or non-aqueous medium using suspending agents. Solid particles include microspheres, microcapsules, nanoparticles and nanospheres.

Emulsions are defined as dispersions of one liquid in another, stabilized by an interfacial film of emulsifiers such as surfactants and lipids. Despite their long history, emulsions are used less often today than other dosage forms due to their inherent instability. Emulsion formulations include water-in-oil and oil-in-water emulsions, multiple water/oil/water emulsions, microemulsions, microdroplets, and liposomes.

A microemulsion is a transparent or substantially transparent emulsion which is formed spontaneously or substantially spontaneously when its components are brought into contact. Microemulsions are thermodynamically stable and contain dispersed particles or droplets of a diameter less than about 200 nm, more preferably less than about 150 nm. These particles may be spherical, although other structures are possible, such as liquid crystals with lamellar, hexagonal or isotropic symmetries.

Microemulsions can also be used as a "microemulsion preconcentrate," defined herein as a composition which spontaneously forms a microemulsion in an aqueous medium, for example, in water upon dilution, or in the gastric juices after oral application. The microemulsion can be diluted in water at a ratio of about 1:1 to about 1:10 by volume.

While emulsion-based delivery systems are useful for certain applications, the delivery vesicles are subject to physical rupture because of the delicate nature of the liquid/membrane/liquid structure. Emulsion based delivery systems also have relatively short release times. Further, it is difficult to isolate emulsion based vesicles from the aqueous media used for storage for subsequent reconstitution.

In spite of these difficulties, microemulsions have been used as successful delivery systems for certain types of pharmaceutical compounds, particularly compounds such as members of the cyclosporin class, which are cyclic oligopeptides. This carrier generally contains a hydrophilic solvent, such as liquid polyethylene glycol (PEG) 200-600, ethylene or propylene glycol, ethanol or propanol, glycerin, water, soluble fatty acid $C_6$-$C_{18}$ esters of sucrose, dimethylisosorbide ethyl-acetate, glycofurol (fatty acid derivative of a cyclic polyol), PEG derivatives of tocopherol, or PEG-fatty acid esters; and a surfactant, such as TWEEN™ 20 (ICI Americas, Inc.) which is polyoxyethylene sorbitan monolaureate. Other ingredients include various PEG (polyethylene glycol) derivatives or phospholipids; a water-insoluble oil such as corn oil, other oils from plants and mixtures of oils; and CREMOPHOR® (BASF Corp.), which is ethoxylated castor oil, and similar PEG derivatives of castor oil or other fats which are used as an amphiphilic solvent, emulsifier, surfactant, etc.

The microemulsions described above are typically droplets of oily material dispersed in water. Liquid droplets have limited stability and may rupture in response to changes in pH, ionic strength, or temperature.

It is therefore an object of this invention to provide microemulsions of fenoldopam and methods for making them with increased stability.

A formulation containing fenoldopam, and methods of making and using the formulation are described herein. The formulation is formed by adding a pre-suspension concentrate composition to an aqueous medium. Upon contact with the aqueous medium, a solid nanoparticle suspension spontaneously forms. The resulting formulation is in the form of a microemulsion. The concentrate contains an amphiphilic solvent, a pharmaceutically acceptable solid carrier such as a solid fatty acid or ester, a surfactant, and fenoldopam or its derivative. Preferably, the concentrate contains a combination of a surfactant with a high hydrophilic/lipophilic balance (HLB) of at least about 8 and a surfactant with a low HLB of less than about 5. These particulate systems can be formulated into topical ointments and creams, oral formulations when loaded into gelatin capsules, or mixed with water for injection for parenteral administration, iv, im or intratumoral injections.

Orally and parenterally administered treatments of fenoldopam mesylate suitable for cancer, or autoimmune diseases or inflammatory diseases having prolonged effectiveness have not been reported. The high effectiveness of fenoldopam mesylate for treating cancer or autoimmune diseases or inflammatory diseases over prolonged periods of time, for repeated or prolonged eradication of detrimental cancer cells or autoimmune cells or other disease-causing cells was not reported. This is so, as fenoldopam mesylate is used in the clinic for its very different ability to bind normal healthy cells of an individual suffering from acute hypertension, and decrease the blood pressure.

This invention proposes an opportunity, for the first time, to successfully conquer this biopharmaceutical hurdle and thus sufficiently improve the care of patients suffering from cancer and immune diseases using fenoldopam in an appropriate delivery system.

DETAILED DESCRIPTION OF PREFERRED EMBODIMENTS

As stated hereinabove, fenoldopam mesylate has been used for treatment of acute hypertension. Fenoldopam mesylate is a highly selective Dopamine D1 receptor agonist, extensively studied and used in the clinic for its vasodilatory actions, mainly in the treatment of severe hypertension, congestive heart failure, and acute and chronic renal failure.

Fenoldopam mesylate does not cross the BBB, and thus has only peripheral actions. Chemically, fenoldopam is 6-chloro-2,3,4,5-tetrahydro-1-(4-hydroxyphenyl)-[1H]-3-benzazepine-7,8-diol methanesulfonate. It has been described in U.S. Pat. Nos. 4,197,297, 4,600,714 and 6,238,693 and is now a generic drug.

Fenoldopam is a racemic mixture with the R-isomer responsible for the biological activity. The R-isomer has approximately 250-fold higher affinity for D1-like receptors than does the S-isomer. Fenoldopam binds but with moderate affinity to α2-adrenoceptors. It has no significant affinity for D2-like receptors, α1 and β adrenoceptors, 5HT1 and 5HT2 receptors, or muscarinic receptors. Prior to the findings of Levite in PCT publication WO2007019266, there has been no evidence that fenoldopam or any other D1 receptor agonist has the ability to kill cancer cells. It has now been shown in PCT publication WO2007019266 that various types of human and animal leukemia and lymphoma, as well as activated T-cells, express highly elevated levels of dopamine D1 receptor as compared to normal resting T-cells that do not express the D1 receptor. It has also been shown therein that fenoldopam, a selective dopamine D1 receptor agonist and other selective dopamine D1 receptor agonists rapidly, potently and selectively kill lymphoma and leukemia of the B-cell, T-cell and non-B non-T (e.g. CML) origin, and normal TCR-activated T-cells. Based on these findings, the invention of that PCT publication was directed to the use of fenoldopam mesylate and other dopamine D1 receptor agonists to selectively kill/eradicate B-cell, T-cell and non-B non-T leukemia and/or lymphoma; activated autoimmune T-cells (or other cells); activated inflammatory T-cells (or other cells); graft rejecting T-cells; and activated GVHD T-cells. It is expected that fenoldopam also has the ability, under certain conditions, to kill/eradicate other cancer cells besides cancer of the B-cell, T-cell and non-B non-T leukemia and/or lymphoma, and other non cancerous cells besides normal activated T-cells, that express the dopamine D1 receptor.

Eradication of such cancer cells or TCR-activated T-cells by several dopamine D1R agonists, including fenoldopam, as described in PCT publication WO2007019266, was shown to occur at several concentrations within a range of 0.1 mM-0.1 nM; rapid: like 'A kiss of death', evident (by release of LDH from the cells) already a few minutes after exposure of the cancer or normal TCR-activated cells to the dopamine D1R agonist; potent: causing death of over 98% of the cells (measured by the number of live and dead cells after 72 hr) and occurring primarily via a mechanism of necrosis.

The present invention presents the preparation of novel lipophilic and hydrophilic complexes, salts, formulations and prodrugs of fenoldopam that possess improved bioavailability and biodistribution and ease of administration for treating tumors that express the dopamine D1 receptor on their cell surface, and that are sensitive to fenoldopam as reported in PCT publication WO2007019266. These lipophilic molecules, incorporated into chylomicrons (CM), are lymphatically absorbed when given with a proper lipid-based formulation. The process of intestinal lymphatic absorption of lipophilic molecules is composed of a cascade of consecutive events that is similar to the absorption of lipophilic dietary constituents and includes uptake of the drug or prodrug molecule into the enterocyte, association of the drug molecule with the triglyceride (TG) core of CM, and transportation of CM with the drug into the lymphatic capillaries. The association of the lipophilic drug with CM is a critical and determining step to ascertain intestinal lymphatic absorption of lipophilic compounds. The degree of association of drugs with the CM within the enterocyte determines what part of the absorbed drug reaches the systemic circulation via the lymphatic system by means of CM and to what extent it enters directly into the portal blood. The association with CM has a potential to reduce the hepatic metabolism of lipophilic prodrug of fenoldopam by targeting the prodrug loaded CM to the lymph instead to the portal blood.

As stated above, it has been surprisingly found that fenoldopam derivatives of the general formula (I) are useful for the treatment and/or prophylaxis of cancer and/or autoimmune diseases and/or inflammatory diseases and/or graft rejection and/or GVHD.

Thus, the present invention provides in one of its aspects a compound of the general formula (I):

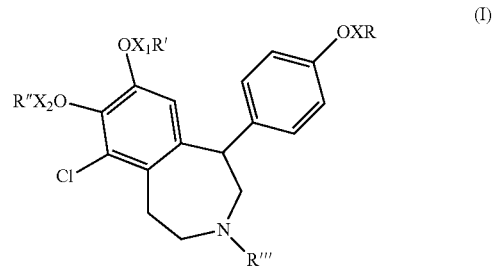

wherein
R, R' and R'', independently of each other, may be H or each independently selected from substituted or unsubstituted, linear or cyclic $C_4$-$C_{25}$ alkyls or ethylene glycol oligomers and combinations thereof. R, R' and R", independently of each other may also be metal ions such as copper or Fe or another suitable metal ion that is safe and forms a complex;

X, $X_1$ and $X_2$, independently of each other, are selected from the group consisting of —C(=O)—O—, —O—C(=O)—O—, —NH—C(=O)—O—, —O—$CR_3R_4$—O—, —C($R_3$)—O—, —O—P(=O)($OR_3$)—O—, wherein the underlined O atom is the corresponding O atom of the fenoldopam skeleton to which said R, R', and R" are bonded; and R''' is an acidic residue that forms a complex salt with the amino group or is bound to the amino group via a biocleavable bond.

Within the context of the present invention, the term "alkyl" refers to a carbon chain containing one or more carbon atoms, preferably 1-25 carbon atoms, which carbon chains may be straight, branched or cyclic. Exemplary alkyl groups herein include, but are not limited to, isobutyl, n-butyl, cyclobutyl, sec-butyl, tert-butyl, pentyl, cyclopentyl, isohexyl, cyclohexyl, and dodecyl. The alkyl group may contain one or more double bond or triple bond which may be part of the carbon chain or appended thereto or may be substituted as defined. The alkyl group is typically connected to fenoldopam via a single bond to the O atom thereof or via an intermediating group or atom. The bond between fenoldopam and the alkyl group may thus be selected amongst an ester bond, a carbonate bond, a urethane bond, an ether bond, an acetal bond, a ketal bond, a hemiacetal bond, a hemiketal bond, and a phosphate bond.

Additionally, the alkyl group may be disrupted by one or more heteroatom or one or more group containing at least one heteroatom, such as an atom selected from N, O, S, P, and a group selected from an ether, a carbonate, a phosphate and an ester.

In one embodiment, in a compound of formula (I), R', R" or R''' is H and the other of $R_2$ or $R_1$ is selected from substituted or unsubstituted $C_4$-$C_{25}$ alkanoyl, a phosphate, a choline group, glycol oligomers, fatty acids and $C_4$-$C_{25}$ triglyceride.

The term "lipophilic" refers within the context of the present invention to the tendency of any one compound disclosed herein to dissolve in fats, oils, lipids, and non-polar solvents such as hexane or toluene. The lipophilicity may arise from the lipophilic character of a part of the compound or of the compound as a whole.

The compounds of the invention may be prepared by chemical binding of the lipophilic tail (i.e., oleic acid or other lipophilic tail) via an ester, ether, amide or other chemical bonds, or via any other bond as defined above, to one or both of the oxygen atoms of the —OH groups in the molecule of fenoldopam. In one embodiment, the bond between fenoldopam and the lipophilic tail is hydrolysable.

For general functional group transformations see for example: *Comprehensive Organic Functional Group Transformations*, Volume 1-7, Second Ed.: A Comprehensive Review of the Synthetic Literature 1995-2003 (Organic Chemistry Series) by Alan R. Katritzky and Richard J. K. Taylor.

In another aspect of the present invention, there is provided the use of a compound of the general Formula (I) for the preparation of a composition. The composition comprising a compound of formula (I) may be any composition known to a person skilled in the art.

In one embodiment, the composition is a pharmaceutical composition.

In another embodiment, the pharmaceutical composition is suited for the treatment and/or prophylaxis of cancer.

The composition of the invention may comprise at least one compound of the general formula (I) or a pharmaceutically acceptable salt or derivative thereof along with a pharmaceutically acceptable carrier, diluent or excipient.

The composition of the modified fenoldopam of this invention may be prepared according to methods known in the art. The composition may be in a form suitable for any route of administration, such as topical, oral, aerosol, intranasal, intraocular, parenteral, subcutaneous, intravenous, intramuscular, intraperitoneal, rectal, and vaginal. Preferably, the composition is suitable for oral administration.

The composition of the invention may be manufactured in various forms such as a sustained release form, a unit dose form, encapsulated, etc.

The compositions of the present invention may be made into various formulations. The requirements for effective pharmaceutical carriers used in such compositions are well known to those of ordinary skill in the art. See "Pharmaceutics and Pharmacy Practice," J.B. Lippincott Co., Philadelphia, Pa., Banker and Chalmers, eds., pages 238-250 (1982), and "ASHP Handbook on Injectable Drugs," Toissel, 4th ed., pages 622-630 (1986).

The term "treatment" as used herein refers to the administration of a therapeutic amount of the composition of the present invention which is effective to treat cancer and/or autoimmune disease and/or inflammatory disease, and/or to prevent or arrest graft rejection and/or prevent or arrest GVHD and/or to treat any other disease—whereby the disease-causing or disease-facilitating cells express the dopamine receptor D1R and whereby the binding of fenoldopam formulations to these dopamine receptors expressed by the detrimental, disease-causing or disease-facilitating cells kills/eradicates these cells rapidly and potently. Thus, in such a mechanism of action, the fenoldopam formulations can be of therapeutic value to all the above mentioned pathologies and others.

As used herein, "concentrate" or "pre-suspension concentrate" generally refers to a composition which spontaneously forms a nanoparticulate dispersion (also referred to herein as "microemulsion") in an aqueous medium, for example in water upon dilution, or in the gastric juices after oral administration. The term "pre-suspension concentrate" includes those compositions that form solid particles having a mean diameter of less than about 500 nm upon contact with an aqueous medium. Dilution of the pre-suspension concentrate in water can be, for example, from about 1:1 fold to about 1:1000 by volume.

As generally used herein, "solid component" includes solid materials that are solid at room temperature (defined herein as 25° C.) and that dissolve in the "pre-suspension concentrate" composition, which upon dispersion in aqueous medium becomes part of the formed solid nanoparticles. Examples of solid components include fatty acids and fatty alcohols and their esters that melt at temperatures above 25° C.; solid polymers; waxes and fats.

As used herein, "solid fat" generally refers to pharmaceutically acceptable carriers which are solid at room temperature as defined above.

As used herein, "lipophilic agents" generally refers to active agents which are slightly soluble in water and which can be delivered in nanoparticles, particularly those active agents having pharmaceutical efficacy.

Composition

A formulation for the administration of lipophilic agents with high bioavailability has been developed. This formulation includes an amphiphilic solvent, which is preferably a lower alkyl ester of lactic acid, a pharmaceutically acceptable solid carrier, such as solid fatty acids and esters, and a surfactant, preferably a combination of a surfactant with a high HLB (hydrophilic/lipophilic balance) of at least about 8 and a surfactant with a low HLB of less than about 5. The hydrophilic solvent is preferably ethyl lactate, propyl lactate, isopropyl lactate, butyl lactate, hexyl lactate, isohexyl lactate, or a mixture thereof. All components are soluble in the amphiphilic solvent to form a homogeneous clear solution.

Other ingredients are optional, including but not limited to, a phospholipid, an ethoxylated fat such as CREMOPHOR® or another similar substance, cationic or anionic lipids such as long chain fatty acids or amines and phospholipidic acids or amines, or a mucoadhesive polymer or a lipid-polyethylene glycol conjugate that will form nanoparticles with surface charged, mucoadhesive, or hydrophilic properties. Optionally, a sufficient amount of the ethoxylated fat such as CREMOPHOR® is substituted for the surfactant.

The preferred particle size in the resultant formulation is preferably less than about 500 nm, more preferably less than about 100 nm, and most preferably from about 5 nm to about 50 nm. In fact, as described in greater detail below, the resultant formulation preferably includes particles sized less than about 100 nm in order to be suitable for the administration of lipophilic agents with effective bioavailability in humans.

The formulations are stable. The formulations have the advantage of not requiring stabilizers, such as antioxidants, for good stability. The excellent stability and the ability to spontaneously form a nanoparticulate suspension are believed to be both due to the use of a combination of amphiphilic solvents such as ethyl lactate and a solid carrier.

Amphiphilic Solvent

The amphiphilic solvent is preferably selected from the family of lower alkyl esters of lactic acid or alternatively from the family of lower alkyl lactone esters or N-methyl pyrrolidone. Hereinafter, the term "lower alkyl" includes $C_1$ to $C_8$ alkyl, for example, methyl, ethyl, propyl, isopropyl and hexyl esters. More preferably, the amphiphilic solvent is methyl lactate, ethyl lactate, propyl lactate, spironolactone or N-methylpyrrolidone.

N-methylpyrrolidone (NMP) is a powerful amphiphilic solvent that dissolves both hydrophilic and hydrophobic compounds such as paclitaxel, steroids, peptides, proteins, saccharides and many polymers including poly(alkyl hydroxyl acids) and PEG derivatives at high concentrations. NMP is miscible with most hydrophilic and hydrophobic solvents including hexanes, ethers, ketones, lipids, alcohols and aqueous solutions. NMP is approved for use in pharmaceutical compositions including injectable formulations. A solution of poly(lactic acid) in NMP and leuprolide is in clinical use for treating prostate cancer.

Ethyl lactate (2-hydroxypropanoic acid ethyl ester) is a colorless liquid which is miscible with water, alcohol and ether. Ethyl lactate is considered to be suitable for human administration with an LD50 which was higher than 5 g/kg in mice when given an oral dose. N-methylpyrrolidone is a colorless liquid which is miscible with water and organic solvents, and is also considered to be safe for human administration. N-methylpyrrolidone is used in the clinic as a solvent for a polymeric in situ implant to treat gingivitis.

Ethyl lactates, and other members of this family of amphiphilic solvents such as propyl lactate, isopropyl lactate, butyl lactate, hexyl lactate and isohexyl lactate, have unexpectedly good properties for the described formulations. For example, ethyl lactate is miscible in both organic and inorganic solvents, since it is more hydrophobic than ethanol. Ethyl lactate is less volatile than ethanol and thus has higher storage stability than ethanol. The properties of the molecule are related to its molecular structure, which features an alcohol group or radical, and an ester group or radical. Without wishing to be limited by a single hypothesis, the dominant functionality of this molecule is related to the alcohol group, which allows the formation of hydrogen bonds, and thus provides hydrophilicity to the molecule. The alcohol group also contains a hydrophobic part, through the carbonyl group of the ester bond, which allows the formation of hydrogen bonds with alcohols. This molecule has the ability to form internal and external hydrogen bonds. The solubilization of the various lipophilic agents to be formulated in the invented formulation can be adjusted by selecting the proper alkyl ester of lactic acid, as the use of longer alkyl residues results in a higher degree of solubilization of the lipophilic agent. The diffusion of alkyl lactates to the water phase is much slower than ethanol, and the diffusion into water from a water free formulation is slower as the alkyl chain of the lactate ester is longer.

In a preferred embodiment, a combination of a solvent selected from the family of lower alkyl esters of lactic acid and a solvent selected from the family of alkyl lactone esters or N-methylpyrrolidone is employed, rather than a single solvent as described above. Optionally, any of these solvents can be combined with other hydrophilic organic solvents such as ethylene glycol, glycofurol or PEG 400.

Surfactant

A suitable surfactant is preferably a combination of a surfactant with a high HLB (hydrophilic/lipophilic balance) of at least about 8 and a surfactant with a low HLB of less than about 5. The term "HLB" refers to the hydrophilic/lipophilic balance of a surfactant. A surfactant with high HLB is hydrophilic, while a surfactant with low HLB is hydrophobic. Therefore, the combination of a surfactant with high HLB and a surfactant with low HLB, is actually a combination of a hydrophilic surfactant and a hydrophobic surfactant.

Particularly preferred combinations of these surfactants feature a large difference between the HLB of the low HLB surfactant and that of the high HLB surfactant. Therefore, one example of such a particularly preferred combination is a combination of TWEEN™ 20 and SPAN™ 80, which is sorbitan monolaurate, although other such combinations could be also be used. SPAN™ hydrophobic surfactants are a group of sorbitan fatty acid esters such as sorbitan monooleate, sorbitan monopalmitate, sorbitan monostearate, sorbitan tristearate, sorbitan monooleate, sorbitan trioleate and sorbitan monolaurate. SPAN™ 80 is an example of a low HLB surfactant, with an HLB of 4.3, and is sorbitan monooleate. SPAN™ hydrophobic surfactants are commercially available from various producers, including Capital City Products, Croda Chem, ICI, Lippo Chem. and Atlas, under various commercial names: ARLACEL™, ARMOTAN, CRILL, EMSORB™, LIPOSORB™, PROTACHEM, and SORBESTER.

Illustrative, non-limiting examples of suitable surfactants from this group, with HLB values given in parentheses, are as follows: SPAN™ 60 (4.7), SPAN™ 65 (2.1), SPAN™ 80 (4.3), SPAN™ 85 (1.8), ARLACEL™ 83 (3.7), ARLACEL™ ITM C (1.7), ARLACEL™ 85 (1.8), ARLACEL™ 80 (4.3), and ARLACEL™ 60 (4.7). These molecules are generally soluble in oil. They are also soluble in most organic solvents. In water they are generally insoluble but dispersible. Other low HLB surfactants include but are not limited to PEG-6 glyceryl monooleate (HLB of about 3 or 4), and propylene glycol laurate (HLB of 4).

TWEEN hydrophilic surfactants (polysorbates) are a family of PEG sorbitan esters (polyoxyethylene-sorbitan-fatty acid esters), for example mono- and tri-lauryl, palmityl, stearyl and oleyl esters of the type known and commercially available under the trade name TWEEN. TWEEN® 20 (polyoxyethylene (20) sorbitan monolaurate) has an HLB of 16.7. Other types of TWEEN® (ICI Americas Inc.) surfactants may also be useful for the compositions disclosed herein.

TWEEN® surfactants are soluble in water but not in oil. The chemical structure of this family of surfactants features one, two or three short PEG chains, generally of about 5 to 20 ethylene glycol units, connected by an ester bond to sorbitan. These surfactants are produced by various companies (Croda, ICI, Sandoz, Mazer, Atlas) and may appear under various trade names, besides TWEEN: SORLATE™, MONITAN™, CRILLET™ and so forth. Members of this family which are polysorbates 20, 21, 30, 60, 61, 65, 80 and 85 have an HLB between 11 and 16.7, and therefore would optionally be suitable as high HLB surfactants.

Other suitable high HLB surfactants may be obtained from manufacturers such as Gattefosse Ltd., and include but are not limited to, sucrose fatty acid esters such as saccharose monopalmitate (HLB of 15) and saccharose monostearate (HLB of 11) or PEG-32 glyceryl laurate (HLB of 14). Suitable high HLB nonionic surfactants include but are not limited to polyethylene glycol (PEG) n-alkanol esters of the Brij family such as Brij 99 which has an HLB in the range of 12.4 to 16.9. Brij 56 is polyoxyethylene [10] cetyl ether and is an example of such a high HLB surfactant which can be substituted for TWEEN 20 or CREMOPHOR. Brij 56 has an HLB of 12.9.

Phospholipid

In an alternative embodiment, a phospholipid is incorporated into the formulation. A phospholipid is a phosphorylated diacylglyceride molecule or its derivative. The parent structure is diacylglycerol phosphate, or phosphatidic acid. Phosphatidyl choline (lecithin) is the choline ester of phosphorylated diacylglyceride. Synthetic lecithins are available with acyl chain lengths ranging from 4 to 19 carbons. The preferred lecithins for biological applications are those with alkyl chain lengths in the biological range (10 to 18 carbons). Naturally occurring lecithin can be obtained from a variety of sources such as egg, bovine heart, or soy bean. Unsaturated lecithins (dioleoyl; dilinoleoyl; alpha-palmitoyl, beta oleoyl; alpha palmitoyl, beta linoleoyl; and alpha oleoyl, beta palmitoyl), dianachidonyl lecithin (highly unsaturated and a prostaglandin precursor), and alpha palmitoyl beta myristoyl lecithin are also available. Certain phospholipids, such as phosphatidic acid, phosphatidyl serine, phosphatidyl inositol, cardiolipin (diphosphatidyl glycerol), and phosphatidyl glycerol, can react with calcium in serum, causing aggregation or the binding of liposheres to cell membranes.

These unfavorable reactions can be minimized by combining these phospholipids with non calcium-binding phospholipids such as phosphatidylcholine. Phosphatidic acid can be isolated from egg or prepared synthetically (dimyristoyl, dipalmitoyl and distearoyl derivatives are available from Calbiochem). Bovine phosphatidyl serine is also available commercially (Sigma Chemical Co. St. Louis, Mo.). Phosphatidyl inositol can be isolated from plant or bovine sources. Cardiolipin can be purified from bovine or bacterial sources. Phosphatidyl glycerol can also be purified from bacteria. All are commercially available.

Pharmaceutically Acceptable Solid Carrier

In a preferred embodiment, the formulation includes a pharmaceutically acceptable solid carrier which can be a fatty acid ester, fatty acid, fatty alcohol or fatty amine, or a polymer. One non-limiting example of a fatty acid ester is tricaprin. Tricaprin is a hydrophobic triester of glycerol and caproic acid. Tricaprin does not dissolve in water and thus remains as a component of the dispersed lipophilic drug-loaded particles after dispersion in aqueous solution. Tricaprin solubilizes many lipophilic agents in a fatty medium which is dispersed by the hydrophilic-hydrophobic dispersing agents. Other such fatty components which are suitable as replacements for tricaprin include, but are not limited to, pure and mixed alkyl esters of fatty acids and mixtures thereof. Examples include ethyl esters of fatty acids such as ethylstearate and ethylpalmitate; and triglycerides such as trilaurin and trimyristin. Mixtures of fats include hydrogenated vegetable oils. The preferred fats are those that solubilize lipophilic agents with a melting point above 25° C., such that the resultant pre-suspension concentrate formulation forms a nanodispersion of solid particles. Wax compositions of long chain fatty acid esters of long chain alcohols are also suitable. Biopolymers such as polycaprolactone, polylactide, poly (lactide-glycolide), and poly(hydroxy butyrate) can be used as solid carrier to form the nano-suspension. The solid carrier can be formed in situ when the oily composition is mixed in an aqueous medium either by chemical reaction induced by reagents in the pre-suspension oily composition or in the aqueous phase or by reacting with the aqueous phase.

Suitable mucoadhesive ingredients that may be added to the pre-suspension concentrate liquid formulation, in order to form nanoparticles with mucoadhesive surface properties include, but are not limited to, hydroxypropyl cellulose derivatives, poly(vinyl alcohol) derivatives, alginates, hyaluronan, and other molecules that have specific adhesive properties to mucosal tissue.

Method of Making the Composition a. Pre-Suspension Concentrate

A pre-suspension concentrate is prepared by dissolving the fenoldopam free base lipophilic agent in a water-miscible organic solvent to form a mixture. Optionally, the solvent is approved for oral use or for injection. The phospholipid is dissolved in this mixture, with gentle heating and mixing. The surfactant and solid material are added and dissolved in the mixture to form an oily, transparent and homogeneous solution. The pre-suspension concentrate has a small volume. When the pre-suspension concentrate is added to aqueous solution, it is spontaneously dispersed to form a dispersion.

b. Nanoparticles

A liquid oily pre-suspension concentrate of a reactive monomer or oligomer may be added to an aqueous solution to spontaneously form a nanodispersion. Optionally, the pre-suspension concentrate features one or more catalysts or curing agents that solidify the nanodispersion to a nanosuspension upon interaction with the aqueous medium. For example, a clear solution of lauryl methacrylate, benzoyl peroxide, TWEEN™ 80, SPAN™ 20, and ethyl lactate are added with mixing to hot water (e.g., above room temperature, for example 70° C.). The oily solution is spontaneously dispersed into a nanodispersion where the nanodispersion is converted to solid nanoparticles as a result of radical polymerization initiated by the contact with the hot water.

In other cases, a phase change may take place to in situ formation of nanoparticulate suspension due to interaction with water, pH, ionic strength, or temperature change. For example, ricinoleic acid based polyanhydrides and polyesters that are liquid at room temperature and above that upon addition to aqueous medium solidify to solid or semi solid mass due to interaction with water. Another example is a copolymer of polyethylene glycol (PEG) and polylactic acid (PLA) that are liquid at room temperature but solidify at temperatures above 30° C. Mixing pre-suspension solutions containing these phase change PEG-PLA with aqueous medium at 30° C. or above causes a nanosuspension to be formed in water.

Polymeric Delivery Systems

Polymeric injectable extended release formulations for intratumoral or intramuscular or subcutaneous administration of fenoldopam have been developed. These systems constantly release the drug over periods from a few days to a few months.

In situ depot forming systems for parenteral controlled drug delivery are typically in the form of liquids or pastes having a wide range of viscosities. Such systems usually contain a biodegradable carrier dissolved or dispersed in a solvent/cosolvent system, while the drug is either dispersed or dissolved in the liquid phase of the delivery system. Upon subcutaneous or intramuscular injection, a solid depot is formed at the site of injection. The administration of such a system is far less invasive and costly than the surgical procedures which are often required for implantation. Different in situ depot forming systems have recently been reviewed and classified into different categories according to the depot forming mechanism (Hatefi et al., *J. Control. Release* 80 (1-3):9-28 (2002)).

The objective of drug therapy is to maximize the therapeutic effect of the drug while minimizing adverse effects. Systemic delivery of drugs to localized tumors has the disadvantage of providing relatively low concentrations of the drug at proliferating cell boundaries which may be located far from the abnormal capillary networks in the tumor. Polymer-based anticancer drug loaded implants provide an opportunity to deliver high, localized doses of drug for a prolonged period directly into a tumor or at the site of tumor resection. Thus, injectable in situ setting semi-solid drug depots are being developed as alternative delivery systems. These implant systems are made of biodegradable products, which can be injected via a syringe into the body and once injected, gel to form a semi-solid depot. Biodegradable polyanhydrides and polyesters are useful materials for controlled drug delivery.

Ricinoleic acid and castor oil containing polyesters and polyanhydrides, which can be adapted for use as fenoldopam carriers, have been described (U.S. Patent Application Publication Nos. 2004/0161464, and 2004/0161464 to Domb). Biodegradable carriers synthesized from ricinoleic acid oligoesters and aliphatic molecules having at least one carboxylic acid and at least one hydroxy or carboxylic acid group that are liquids or pastes at temperatures below 37° C. and methods of making and using thereof can be used for the delivery of fenoldopam. The polymers described herein significantly increase their viscosity upon immersion in aqueous medium. The polymers made from ricinoleic acid oligoesters are less viscous and easier to inject compared to polymers of similar composition and molecular weight prepared from ricinoleic acid monomers, possess a higher molecular weight, retain an incorporated drug for longer periods, and degrade into soft degradation products at a slower rate compared with polymers synthesized from ricinoleic acid monomers.

Hydrophilic based injectable formulations for controlled drug release are also useful for localized or systemic fenoldopam extended delivery. Such formulations include copolymers of lactide and ethylene glycol (PLA-PEG), block copoly(ethylene glycol-propylene glycol), and branched PEG which all provide a solution at room temperature and solidify at body temperature in the injection site and deliver the loaded fenoldopam over time.

Fenoldopam for Drug Targeting and Cell Separation and Sorting.

Particles loaded with active agents, either cancer drugs or anti-inflammatory agents, for use in drug targeting, are prepared by binding fenoldopam to the particle surface during preparation of the particle, such as when using copolymers of a hydrophobic chain attached to a hydrophilic segment to which fenoldopam is bound. Upon formulation of these block copolymers, the hydrophilic moiety is exposed at the outer surface of the particle and is available for interaction with suitable receptors on tissue or cells. Particles can gain fenoldopam targeting capabilities by coating them with a polymer conjugate of fenoldopam which has affinity to certain particle surfaces. For example, PLA particles loaded with paclitaxel can be coated with hydrophobized fenoldopam conjugated dextran or arabinogalactan. The conjugates are prepared by reductive amination of the polysaccharide or conjugation via an ester, amide or ether bond. When magnetic nanoparticles are to be coated, polysaccharides possessing bound fenoldopam and hydrophobic side groups, such as fatty chains, are applied to the particle surface from the proper solution and incubation conditions.

It should be understood that, while the new formulations of the present invention are designed primarily for the new indications disclosed in PCT publication WO2007019266, it is expected that such formulations will also be better than fenoldopam mesylate itself for the original indications of anti-hypertension, renal failure, etc., causing vasodilation in various conditions, etc. Thus, each of the pharmaceutical formulations of the present invention may be used for regulating blood pressure and treating severe hypertension, and kidney failure and kidney disorders and myocardial infarction resulting from hypertension.

EXAMPLES

Materials methyl lactate, ethyl lactate, propyl lactate, isopropyl lactate, butyl lactate and 2-ethylhexyl lactate were obtained from Purac Biochem, The Netherlands. Trilaurin was obtained from Lipo Chemicals Inc., Patterson, N.J. Tricaprin was obtained from Sasol, Germany GmbH. TWEEN 80 and SPAN 20 were obtained from Sigma Chemical Co., St. Louis, Mo. L-Phosphatidylcholine 95% was obtained from Avanti Polar Lipids, Inc., Alabaster, Ala.

In these non-limiting examples, formulations of fenoldopam (5% w/w) together with tricaprin or trilaurin, phospholipid (L-α-phosphatidylcholine, 95%, egg) and TWEEN™ 80, SPAN™ 20 and/or ethoxylated castor oil were dissolved in lactate esters.

Examples 1 and 2

Effects of TWEEN and Fatty Component on Particle Size

Tables 1-2 summarize the particle size (radius) of formulations prepared by the pre-concentrate method. The influence of each component, and the effect of changing the amount and/or replacing the component, were examined.

The difference in particle size of the formulation with and without an emulsifier, TWEEN™ 80, is shown in Table 1. The particle size is smaller when TWEEN™ 80 is incorporated into the formulation.

Table 2 shows that decreasing the concentration of the fatty component decreases the particle size.

While the results are not shown, increasing the concentration of TWEEN™ 80 does not significantly affect the particle size.

TABLE 1

Fenoldopam Pre-concentrate Formulations
Using TWEEN ™ 80 as an Emulsifier

|  | 1 | 2 | 3 | 4 |
|---|---|---|---|---|
| fenoldopam (mg) | 3 | 3 | 3 | 3 |
| Tricaprin (mg) | 5 | — | — | — |
| Trilaurin (mg) | — | 5 | 5 | 5 |
| PL egg (mg) | 2.5 | 2.5 | 2.5 | 2.5 |
| TWEEN ™ 80 (mg) | — | — | 4 | 10 |
| SPAN ™ 80 (mg) | — | — | — | — |
| Ethyl lactate (mg) | 40 | 40 | 33 | 31 |
| Mean Particle size after dispersion (nm) | 250 | 210 | 60 | 60 |

TABLE 2

The Effect of Concentration of the Fatty Component
on Particle Size of Fenoldopam Pre-Suspension
Concentrate Formulations

|  | E-99-1 | A-99-2 | A-99-3 |
|---|---|---|---|
| fenoldopam (mg) | 3 | 3 | 3 |
| Trilaurin (mg) | 2.5 | 5 | 2.5 |
| PL egg (mg) | 2.5 | 2.5 | 1 |
| TWEEN ™ 80 (mg) | 20 | 20 | 20 |
| SPAN ™ 80 (mg) | — | — | — |
| NMP (mg) | 20 | 20 | 20 |
| Mean Particle size after dispersion (nm) | 60 | 70 | 50 |

Example 3

Stability of Pre-Suspension Concentrate Formulations

Selected pre-suspension concentrate formulations were incubated at 37° C. for 30 days in glass vials with sealed plug for stability studies. The surface morphology of liposheres before and after incubation was studied by Transmission Electron Microscopy. The particle size before and after incubation was determined by an ALV-NIBS/HPPS, high performance particle size analyzer.

When administering a fenoldopam dispersion of 60 nm particle size, improved bioavailability is obtained.
Synthesis of Lipophilic Prodrugs of Fenoldopam.

Esters of fenoldopam were prepared by dissolving the drug in an organic solvent such as ethyl acetate or chloroform and adding to the solution the acyl chloride derivative in the presence of poly(vinyl pyridine) beads as HCl collecting agent. The reaction takes place at room temperature overnight where the solution is filtered and evaporated to dryness. The residue was purified by silica chromatography or by dissolving in propylene glycol or THF and precipitation in water. Acyl chloride derivatives of octanoic acid, dodecanoic acid, oleic acid and stearic acid were reacted with fenoldopam at 1, 2, and 3 equivalents to obtain mono di and tri substitutions of the phenol groups. In all reactions, high yields of over 70% were obtained with a mixture of esters which were separated to the individual derivative by chromatography. To better control the derivatization, the ortho phenol groups were protected by a complex or acetal formation to allow reaction on the third phenolic group.

Similarly, chloroformate derivatives of fatty alcohols were reacted with the drug to form the carbamate derivatives.

Metal complexes are prepared from the reaction of, for example, an aqueous solution of copper chloride with propylene glycol solution of fenoldopam mesylate to allow complexation to the phenolic groups.

Phenolate salts of the drug are prepared by mixing a morpholine or piperidine into a fenoldopam solution in ethyl acetate. After mixing, salts were obtained.

Example 4

Liquid Polyesters Containing Ricinoleic Acid (RA)

The hydroxyl RA was used as initiator for the ring opening polymerization of DL-lactide, caprolactone and glycolic acid and their mixtures. ABA triblock copolymers with B segment being ricinoleic acid were obtained by ring opening polymerization of HO terminated RA oligomers with DL-lactide using stannous octoate as catalyst. The molar ratio between the RA oligomer and lactide determined the polymer molecular weight and segment length. Triblock copolymers of DL-lactide containing 20% RA oligomers were liquid at room temperature and form a gel in water. Similarly, pasty polymers were obtained from diblock copolymers of DL-lactide and RA oligomers having one hydroxyl group.

Random copolymers of RA oligomers and hydroxyl acids were obtained by polycondensation of ricinoleic acid oligomers with lactic acid, glycolic acid, hydroxyl butyric acid and the like. The polymerization is taking place in toluene with acidic catalysis. After toluene evaporation, the polymerization continues at 130° C. under 1 mm Hg vacuum to yield a pasty polymer at a less than 10% lactic acid content.

Random copoly(ester anhydride) of ricinoleic acids and sebacic acid were prepared from the reaction of ricinoleic acid and poly(sebacic anhydride) to form sebacic anhydride oligomers terminated with ricinoleic acid followed by anhydride polymerization using acetic anhydride as coupling agent under high vacuum. Various copolymers were obtained from the copolymerization of hydroxy acids and their lactones into polyesters and polyanhydrides with ricinoleic acid or castor oil. These polymers increase in viscosity when injected in the body and release an incorporated drug including fenoldopam for weeks and months, depending mainly on the polymer composition and drug loading. In a typical experiment, pasty poly(ricinoleic acid sebacic acid) 3:7 w/w ratio, molecular weight 4.500, was mixed with powdery fenoldopam (20% w/w) until a uniform pasty mixture was obtained. The formulation was loaded into a glass 1 ml syringe. Stability of the formulation was determined periodically for injectability and drug content as well as drug release rate. The in vitro release was determined in 0.1M phosphate buffer pH7.4 at 37° C. where a drop of the formulation (100 mg) was injected into 10 ml solution and the drug concentration in the solution was determined by UV or HPLC. C18-column 5.4☐25 cm with a 1:4 v/v ratio of methanol and 0.025 M sodium phosphate monobasic, monohydrate buffer pH 2.5 Run conditions: flow 1 ml/min; run time: 10 min; UV detection at 225 nm. Samples from dissolution testing are injected as obtained and solid samples were dispersed in either buffer pH 2.5 or the HPLC eluent. A constant release for at least 4 weeks was obtained. No change in the formulation appearance, fenoldopam content and uniformity, release profile and injectabilty after 6 months at 4° C. was observed.

Example 5

IV Injectable Formulations

Injectable formulations that can be delivered IV need to have nanometer up to micron size particles that can be injected without blocking the blood vessels. Liposomal formulations are prepared by formulating free base fenoldopam into liposomal formulation using acidic and non-charged phospholipids having PEG side groups that will show on the liposomal formulation. Nanoparticles loaded with the drug are prepared from stereocomplexation in the presence of the free base drug using D- and L-PLA solutions.

We claim:

1. A non-infusion pharmaceutical formulation, comprising a composition formulated for delivery of fenoldopam or a derivative of fenoldopam to the human body, which comprises particles of a size of about 5 to 500 nm in an aqueous medium, comprising:
   (i) at least one surfactant;
   (ii) at least one solid component which is a solid at room temperature;
   (iii) an amphiphilic solvent; and
   (iv) a compound of the formula

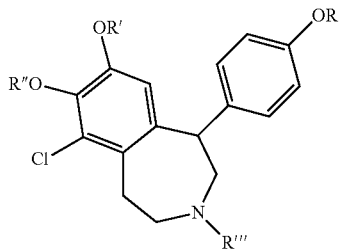

wherein either (i) R, R', R" and R'" are H or (ii) R, R' and R" are the same or different residues that form an electrostatic salt with the phenolate anion, a metal ion or organometallic molecules that form a complex with one or more phenolic groups, or an organic residue covalently bound to the phenolic residue via a bio-cleavable ester or carbonate bond, and R'" is a specific residue that forms an electrostatic salt with the amine, a metal ion or atom or an organic residue covalently bound to the amino residue via a bio-cleavable amine, amide, or urea bond.

2. The pharmaceutical formulation of claim 1, which are dosage forms for oral, topical, parenteral, intratissue, targeting and controlled release of fenoldopam.

3. The pharmaceutical formulation of claim 1, wherein the amphiphilic solvent is selected from the group consisting of alkyl esters of lactic acid, alkyl esters of glycolic acid, and N-methyl pyrrolidine.

4. The pharmaceutical formulation of claim 3, wherein the lower alkyl lactic acid ester is ethyl lactate.

5. The pharmaceutical formulation of claim 1, wherein the solid component is selected from the group consisting of fatty acid esters, polymers, fatty acids, fatty alcohols, fatty amines, paraffins, waxes, partially hydrogenated vegetable oil, fully hydrogenated vegetable oil and combinations thereof.

6. The pharmaceutical formulation of claim 1, wherein the solid component is a compound that solidifies in situ upon dispersion in the aqueous medium.

7. The pharmaceutical formulation of claim 1, wherein the solid component is a phase change polymer that solidifies due to a change in temperature, pH or ionic strength or interaction with water molecules.

8. The pharmaceutical formulation of claim 3, wherein the surfactant is a mixture of two surfactants wherein one surfactant is a high hydrophilic/lipophilic balance (HLB) surfactant having an HLB of at least about 8, and the second surfactant is a low HLB surfactant having an HLB of less than about 5.

9. The pharmaceutical formulation of claim 1, wherein the surfactant is selected from the group consisting of polyoxyethylene (20), sorbitan monolaurate, sorbitan monooleate and combinations thereof.

10. The pharmaceutical formulation of claim 1, wherein the composition further comprises polyethyleneglycol-hydrogenated castor oil.

11. The pharmaceutical formulation of claim 1, wherein the composition further comprises a phospholipid selected from the group consisting of egg phospholipids, soy phospholipids, lecithin and combinations thereof.

12. The pharmaceutical formulation of claim 1, wherein the composition further comprises a fatty acid ester.

13. The pharmaceutical formulation of claim 1, wherein the particle size is about 5 to 100 nm.

14. The pharmaceutical formulation of claim 12, wherein the particle size is in a range of from about 5 nm to about 50 nm.

15. The pharmaceutical formulation of claim 1, wherein one or more of the phenol groups are complexed with metal ions and metal atoms.

16. The pharmaceutical formulation of claim 1, wherein the amino group forms a salt with polyacids and wherein the polyacids are selected from the group consisting of hyaluronic acid, carboxymethyl cellulose and alginic acid.

17. A non-infusion pharmaceutical formulation for delivery of fenoldopam to the human body, which is in a dosage form of a pasty polymer with fenoldopam mixed in, wherein the polymer is a hydrophilic or hydrophobic polymer that increases its viscosity at the injection site in the body.

18. The pharmaceutical formulation of claim 17, wherein the polymer is a poly(ricinoleic acid-sebacic acid) copolymer with fenoldopam mixed in.

19. The pharmaceutical formulation of claim 17, wherein the polymer is a polyester made from ricinoleic acid and/or castor oil and an alkyl hydroxy acid with fenolopam mixed in.

20. The pharmaceutical formulation of claim 2, which is a polymer composition that releases fenoldopam for periods from 2 days to several months.

21. The pharmaceutical formulation of claim 7, wherein the phase change polymer is selected from the group consisting of a copolymer of lactide and ethylene glycol (PLA-PEG), a block copolymer of ethylene glycol and propylene glycol, and branched PEG.

* * * * *